(12) United States Patent
Trautman et al.

(10) Patent No.: US 6,322,808 B1
(45) Date of Patent: Nov. 27, 2001

(54) DEVICE FOR ENHANCING TRANSDERMAL AGENT FLUX

(75) Inventors: Joseph Creagan Trautman, Sunnyvale; Patrick S.-L. Wong, Burlingame; Peter E. Daddona, Menlo Park; Hyunok Lynn Kim, Walnut, all of CA (US); Michael G. Zuck, Bend, OR (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/208,813

(22) Filed: Dec. 9, 1998

(51) Int. Cl.[7] .............. A61K 9/70; A61K 9/22; A61M 31/00; A61M 5/00

(52) U.S. Cl. .............. 424/448; 424/449; 604/46; 604/47; 604/48; 604/49; 604/51; 604/117; 604/181; 604/290; 604/890.1

(58) Field of Search .................. 424/400, 402, 424/448, 449; 604/46–49, 51, 117, 181, 289, 290

(56) References Cited

U.S. PATENT DOCUMENTS

| | | | |
|---|---|---|---|
| Re. 25,637 | 9/1964 | Kravitz et al. | 128/253 |
| 2,893,392 | 7/1959 | Wagner et al. | 128/253 |
| 3,072,122 | 1/1963 | Rosenthal | 128/253 |
| 3,675,766 | 7/1972 | Rosenthal | 206/63.4 |
| 3,814,097 | 6/1974 | Ganderston et al. | 128/268 |
| 3,964,482 * | 6/1976 | Gerstel et al. | 128/260 |
| 4,340,048 | 7/1982 | Eckenhoff | 128/213 |
| 4,379,454 | 4/1983 | Campbell et al. | 604/897 |
| 4,588,580 | 5/1986 | Gale et al. | 424/21 |
| 4,655,766 | 4/1987 | Theeuwes et al. | 604/896 |
| 4,698,062 | 10/1987 | Gale et al. | 604/896 |
| 4,753,651 | 6/1988 | Eckenhoff | 424/449 |
| 4,756,314 | 7/1988 | Eckenhoff et al. | 128/760 |
| 4,832,953 | 5/1989 | Campbell et al. | 424/448 |
| 4,867,982 | 9/1989 | Campbell et al. | 424/449 |
| 5,080,646 | 1/1992 | Theeuwes et al. | 604/20 |
| 5,147,296 | 9/1992 | Theeuwes et al. | 604/20 |
| 5,169,382 | 12/1992 | Theeuwes et al. | 604/20 |
| 5,169,383 | 12/1992 | Gyory et al. | 604/20 |
| 5,242,406 | 9/1993 | Gross et al. | 604/132 |
| 5,250,023 | 10/1993 | Lee et al. | 604/20 |
| 5,268,209 | 12/1993 | Hunt et al. | 428/34.3 |
| 5,279,543 | 1/1994 | Glikfeld et al. | 604/20 |
| 5,279,544 | 1/1994 | Gross et al. | 604/20 |
| 5,310,404 | 5/1994 | Gyory et al. | 604/20 |
| 5,312,456 | 5/1994 | Reed et al. | 411/456 |
| 5,362,307 | 11/1994 | Guy et al. | 604/20 |
| 5,385,543 | 1/1995 | Haak et al. | 604/20 |
| 5,423,739 | 6/1995 | Phipps et al. | 604/20 |
| 5,438,984 | 8/1995 | Schoendorfer | 128/632 |
| 5,569,272 | 10/1996 | Reed et al. | 606/151 |
| 5,879,326 * | 3/1999 | Godshall et al. | 604/51 |

FOREIGN PATENT DOCUMENTS

| | | | |
|---|---|---|---|
| 195 25 607 A1 | 1/1997 | (DE) | A61M/31/00 |
| WO 96/17648 | 6/1996 | (WO) | A61N/1/30 |
| WO 96/37155 | 11/1996 | (WO) | A61B/17/20 |
| WO 96/37256 | 11/1996 | (WO) | A61N/1/30 |
| WO 97/07734 | 3/1997 | (WO) | A61B/5/00 |
| WO 97/48440 | 12/1997 | (WO) | A61N/1/30 |
| WO 98/28037 | 7/1998 | (WO) | A61M/37/00 |

OTHER PUBLICATIONS

Haley, Thomas J., et al., Journal of Pharmaceutical Sciences, vol. 63, (1974), pp. 106., "Instrument for Producing Standardized Skin Abrasions".

Eppstein, Jonathan, et al., presented at a conference sponsored by IBC in San Diego on Dec. 15–Dec. 18, 1997, "Rapid Transdermal Drug Delivery with Thermal Micro–Poration".

Reiss, Susan M., Biophotonicks International, May/Jun. 1997, pp. 43–45, "Glucose– and Blood–Monitoring Systems Vie for Top Spot".

* cited by examiner

Primary Examiner—Shelley A. Dodson
(74) Attorney, Agent, or Firm—D. Byron Miller; Owen J. Bates

(57) ABSTRACT

A device (3) comprising a sheet member (6) having a plurality of microprotrusions (4) for penetrating the skin and a rigid support (15) contacting and extending across the sheet member (6) for transmitting an applied force evenly across the length and width of the sheet member (6) to reproducibly and reliably penetrate the skin with the microprotrusions (4).

37 Claims, 9 Drawing Sheets

DEVICE FOR ENHANCING TRANSDERMAL AGENT FLUX

TECHNICAL FIELD

The present invention relates to transdermal agent delivery and sampling. More particularly, this invention relates to the transdermal delivery of agents, such as peptides and proteins, through the skin, as well as the transdermal sampling of agents from the body, such as glucose, other body analytes and substances of abuse, such as alcohol and illicit drugs.

BACKGROUND ART

Interest in the percutaneous or transdermal delivery of peptides and proteins to the human body continues to grow with the increasing number of medically useful peptides and proteins becoming available in large quantities and pure form. The transdermal delivery of peptides and proteins still faces significant problems. In many instances, the rate of delivery or flux of polypeptides through the skin is insufficient to produce a desired therapeutic effect due to their large size/molecular weight and the resulting inability to pass through natural pathways (pores, hair follicles, etc.) through skin. In addition, polypeptides and proteins are easily degradable during penetration of the skin, prior to reaching target cells. Likewise, the passive flux of water soluble small molecules such as salts is limited.

One method of increasing the transdermal delivery of agents relies on the application of an electric current across the body surface or on "electrotransport". "Electrotransport" refers generally to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent. The electrotransport of agents through a body surface may be attained in various manners. One widely used electrotransport process, iontophoresis, involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying a high voltage electrical pulse to a membrane. In many instances, more than one of these processes may be occurring simultaneously to different extents. Accordingly, the term "electrotransport" is given herein its broadest possible interpretation, to include the electrically induced or enhanced transport of at least one charged or uncharged agent, or mixtures thereof, regardless of the specific mechanism(s) by which the agent is actually being transported. Electrotransport delivery generally increases agent delivery, particularly large molecular weight species (e.g., polypeptides) delivery rates, relative to passive or non-electrically assisted transdermal delivery. However, further increases in transdermal delivery rates and reductions in polypeptide degradation during transdermal delivery are highly desirable.

One method of increasing the agent transdermal delivery rate involves pre-treating the skin with, or co-delivering with the beneficial agent, a skin permeation enhancer. The term "permeation enhancer" is broadly used herein to describe a substance which, when applied to a body surface through which the agent is delivered, enhances its flux therethrough. The mechanism may involve a reduction of the electrical resistance of the body surface to the passage of the agent therethrough, an increase in the permselectivity and/or permeability of the body surface, the creation of hydrophilic pathways through the body surface, and/or a reduction in the degradation of the agent (e.g., degradation by skin enzymes) during electrotransport.

There have been many attempts to mechanically disrupt the skin in order to enhance transdermal flux, such as, U.S. Pat. Nos. 3,814,097 issued to Ganderton et al., 5,279,544 issued to Gross et al., 5,250,023 issued to Lee et al., 3,964,482 issued to Gerstel et al., U.S. Pat. No. Re 25,637 issued to Kravitz et al. and PCT application WO 96/37155. These devices typically utilize tubular or cylindrical structures generally, although Gerstel does disclose the use of other shapes, to pierce the outer layer of the skin. The piercing elements disclosed in these references generally extend perpendicular from a thin flat member, such as a pad or metal sheet. The flexible nature of the flat member and the tubular shape of the piercing elements result in a variety of short-comings, such as manufacturing difficulties, flexing of the flat member when pressure is applied to the top of the device, uneven penetration of the skin, poor puncturing of the skin resulting in low transdermal flux and, for electrotransport, increased irritation due to concentrating the drug flux through fewer pathways.

DESCRIPTION OF THE INVENTION

The present invention provides a device suitable for increasing transdermal flux. The device has microprotrusions which consistently and reliably penetrate a body surface (e.g., skin) to enhance agent delivery or sampling. The device of the present invention can be easily manufactured in high volumes and at low cost. The device of the present invention can penetrate the stratum corneum of skin with a plurality of microprotrusions to form pathways through which a substance such as a drug can be introduced (i.e., delivery) or a substance such as a body analyte can be withdrawn (i.e., sampling). A principal advantage of the present invention is that the device ensures uniform penetration (i.e., generating the same size and depth pathways) by the microprotrusions across the device. Furthermore, the present invention reproducibly provides uniformity in penetration from patient to patient.

In one aspect, the invention comprises a rigid structure which contacts and extends across a flexible device having a plurality of microprotrusions for piercing the skin. The rigid structure transmits force applied to the top of the structure substantially evenly across the flexible device and thus transmits uniform displacement of the microprotrusions. This is accomplished with substantially less dissipation of the application force in the compliant elements of the flexible device having the microprotrusions. The rigid structure provides assured transmittance of an externally applied load to the microprotrusions for easier, complete and reproducible skin penetration. The improved penetration of the skin by the microprotrusions because of the rigid structure is particularly beneficial in producing increased flux. The evenly distributed displacement of the microprotrusions provides nearly complete penetration by all of the microprotrusions so as to produce a substantial number of agent pathways and electrical continuity (if electrotransport is used) with the skin for continued and reproducible agent flux through the skin.

In one aspect of the invention, the flexible skin piercing device comprises a relatively thin flexible sheet which in use is adapted to be placed in substantially parallel relation with the body surface to be pierced. The sheet has a plurality of openings therethrough, which allow the agent to pass between a reservoir associated with the sheet (and typically positioned on the body distal surface of the sheet) and the holes pierced in the body surface by the microprotrusions. The sheet also has a plurality of microprotrusions (also referred to as micro-blades) extending approximately perpendicularly from a body proximal side of the sheet. In this aspect of the invention, a rigid support structure contacts and extends across the sheet in order to impart added structural rigidity thereto and to more evenly distribute any force applied to the device for purposes of more uniformly displacing the microprotrusions into (i.e., to pierce) the body surface. Optionally, though preferably, the rigid structure forms a void for an agent reservoir. The reservoir can be filled with an agent containing/sampling reservoir.

In a second aspect of the invention, the flexible skin piercing device comprises a relatively thin flexible sheet having a configuration defining a void or space for holding an agent-containing or agent-receiving reservoir. In use, the sheet is placed in substantially perpendicular relation with the body surface to be pierced, such that the sheet has a body surface-contacting edge, said edge having a plurality of microprotrusions extending therefrom. In this aspect of the invention, a rigid support structure contacts and extends across the body distal edge of the sheet in order to impart structural rigidity thereto and to more evenly distribute any force applied to the device for purposes of more uniformly displacing the microprotrusions into (i.e., to pierce) the body surface.

The device of the present invention can be used in connection with agent delivery, agent sampling or both. In particular, the device of the present invention is used in connection with transdermal drug delivery, transdermal analyte sampling, or both. Delivery devices for use with the present invention include, but are not limited to, electrotransport devices, passive devices, osmotic devices and pressure driven devices. Sampling devices for use with the present invention include, but are not limited to, reverse electrotransport devices, passive devices, negative pressure driven, and osmotic devices.

The device of the present invention can be used in a repeating manner in order to keep the microcuts/microslits in the body surface, which microcuts/microslits are created by the microprotrusions, open for extended periods of time during transdermal delivery or sampling. This can be easily accomplished by having the patient or other medical technician periodically reapply pressure to the skin distal side of the device, causing the microprotrusions to repierce the stratum corneum layer of the skin. This overcomes potential closing of the initially cut slits due to the body's natural healing processes.

BRIEF DESCRIPTION OF THE DRAWINGS

In the figures, like reference numerals refer to like elements in the several drawings.

MODES FOR CARRYING OUT THE INVENTION

Figure 1:
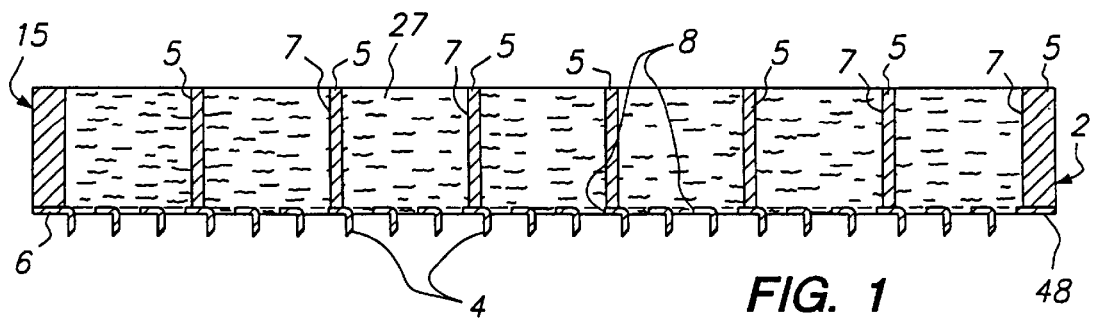
FIG. 1 is an enlarged cross-sectional view of a rigid support and skin penetrating member taken along line 1—1 in FIG. 2.

Turning now to the drawings in detail, the device 2 of the present invention is generally shown in FIG. 1 comprising skin penetrating sheet member 6 and support member 15. Device 2 is used to enhance the transdermal delivery or sampling of an agent. The terms "substance", "agent" and "drug" are used interchangeably herein and broadly include physiologically or pharmacologically active substances for producing a localized or systemic effect or effects in mammals including humans and primates, avians, valuable domestic household, sport or farm animals, or for administering to laboratory animals such as mice, rats, guinea pigs, and the like. These terms also include substances such as glucose, other body analytes that are found in the tissue, interstitial fluid and/or blood, alcohol, licit substances, and illicit drugs, etc. that can be sampled through the skin.

The major barrier to the transdermal flux of agents (e.g., drugs to be delivered and analytes to be sampled) is the outermost layer (i.e., stratum corneum). The inner division of the epidermis generally comprises three layers commonly identified as stratum granulosum, stratum malpighii, and stratum germinativum. There is essentially little or no resistance to transport or to absorption of an agent through the stratum granulosum, stratum malpighii, and stratum germinativum. Device 2 comprises a rigid support member 15 and a compliant sheet member 6 (see FIG. 3 in which device 2 is in an inverted position to show the microprotrusions) having a plurality of microprotrusions 4 extending outwardly therefrom. The device 2 is pressed against an area of skin through which an agent is to be transdermally delivered or sampled. The microprotrusions 4 form tiny slits in the skin and penetrate at least through the stratum corneum so that the agent is conducted through the skin with little or no resistance. Typically, the microprotrusions penetrate the skin to a depth of up to 500 μm, more typically to a depth of 50 to 300 μm. The microprotrusions 4 can be microblades (FIGS. 1 and 3), pins (not shown), or any of a variety of configurations for piercing the skin or body surface. The microprotrusions 4 penetrate the stratum corneum of the epidermis when pressure is applied to the top of the support member 15 to increase the administration of, or sampling of, an agent through a body surface. The term "body surface" as used herein refers generally to the skin, mucous membranes, and nails of an animal or human, and to the outer surface of a plant. The microprotrusions 4 penetrate the body surface to create good agent conduction from the system into the body, or vice versa.

Figure 2:
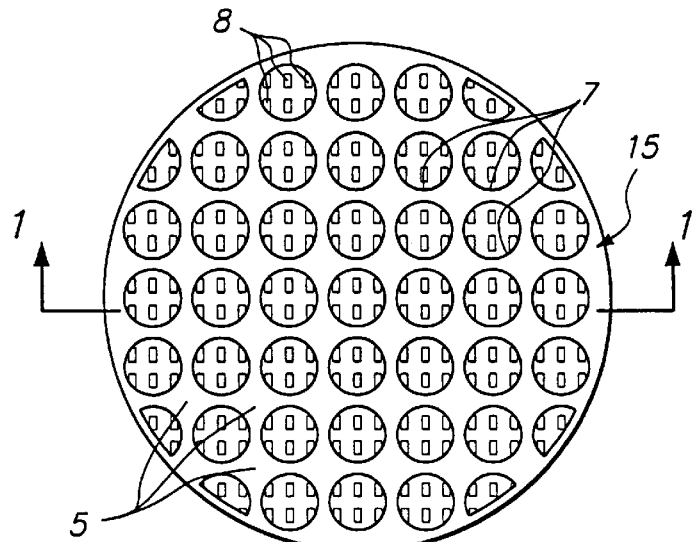
FIG. 2 is a top plan view of the rigid support of FIG. 1.
Figure 3:
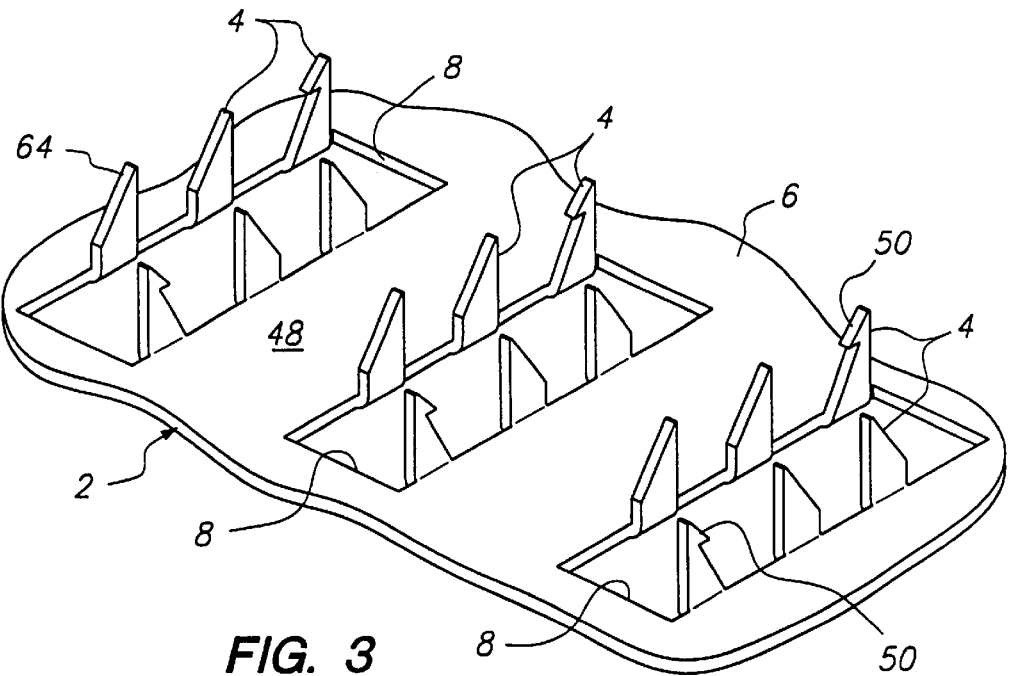
FIG. 3 is an enlarged perspective view of the bottom side of a skin penetrating device with a connecting medium removed therefrom for clarity in accordance with one embodiment of the present invention.
Figure 4:
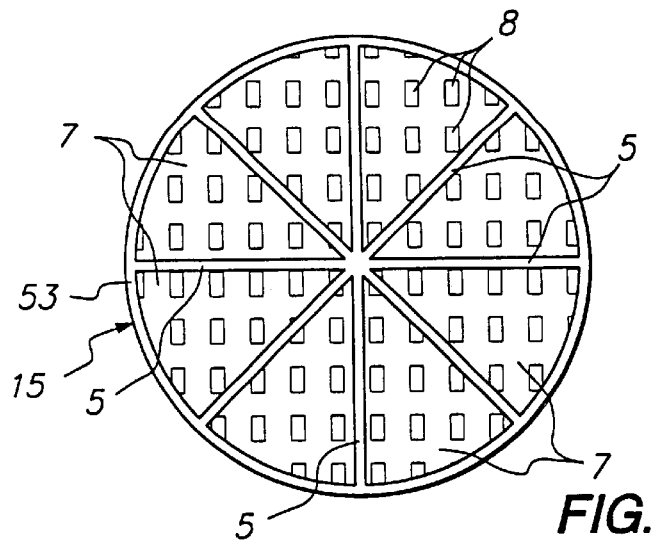
FIGS. 4, 6 and 7 are top plan views of other embodiments of the rigid support.

In the embodiments shown in FIGS. 1–3, the sheet member 6 is formed with a plurality of openings 8, each opening 8 having at least one microprotrusion 4 along the periphery thereof. The microprotrusions 4 cut microslits in the stratum corneum, thereby enhancing the transdermal flux of agent released from or collected in the agent containing or collecting reservoirs 27 housed by the plurality of voids 7.

Sheet member 6 can be composed of metal, silicon or plastic, although metals such as stainless steel and titanium are preferred. Sheet member 6 is generally compliant and flexible because of its relatively thin thickness. For example, when sheet member 6 is comprised of a metal such as stainless steel or titanium, the sheet member 6 will typically have a thickness of only about 5 μm to about 100 μm, and more typically about 25 μm to about 50 μm.

In accordance with the present invention, a rigid structural support member 15 having greater rigidity than the sheet member 6 is placed across the sheet member 6 (FIGS. 1 and 2). The support member 15 prevents deformation or flexing of sheet member 6 as the device 2 is applied to the body surface and a downward force (i.e., directed toward the body surface being pierced) is applied in order to cause the microprotrusions 4 to pierce the body surface. The support member 15 should be sufficiently rigid to deflect less than 300 μm, and more preferably less than 50 μm, under manually applied finger or hand pressing of the device 2 against the skin. Support member 15 can be a variety of configurations, for example but not limited to the embodiments shown in FIGS. 1, 2, 4–8 and 13. In the embodiment shown in FIGS. 1 and 2, support member 15 is a rigid structure which forms a plurality of voids 7, extending through the thickness of the support member, which voids 7 collectively house reservoir 27 (FIG. 1) for containing the agent that is to be delivered or for receiving the agent that is to be sampled. Between the voids 7 are a plurality of supports or cross-members 5 which are in contact with and extend across the width or length of the sheet member 6. The cross-members 5 transmit force that is applied to the top of the device 3 evenly across the sheet member 6 so that each of the microprotrusions 4 are displaced (into the skin) the same amount for more even penetration of the skin by the microprotrusions 4. When used with a transdermal electrotransport device, the sheet member 6 and/or support member 15 are preferably electrically isolated or insulated from the current conducting elements (e.g., the electrodes) of the electrotransport device in order to avoid short circuiting the drug reservoir. This can be achieved by using electrically non-conducting, electrically insulative materials or coatings for sheet member 6 and/or support member 15.

Preferably the support member 15 also has a low compressibility. Optimally, the support member 15 compresses a distance of less than 250 μm, and more preferably less than 50 μm, during manually applied finger or hand pressing of the device against the skin. Most preferably, the support member 15 will exhibit a combined flexibility and compressibility of less than about 250 μm during manually applied finger or hand pressing of the device against the skin.

The support member 15 maybe made from any material having the aforementioned high rigidity, and preferably the aforementioned low compressibility. Suitable materials include metals, metal alloys, ceramics, glasses, rigid plastics, and reinforced (e.g., carbon fiber reinforced).

Figure 7:
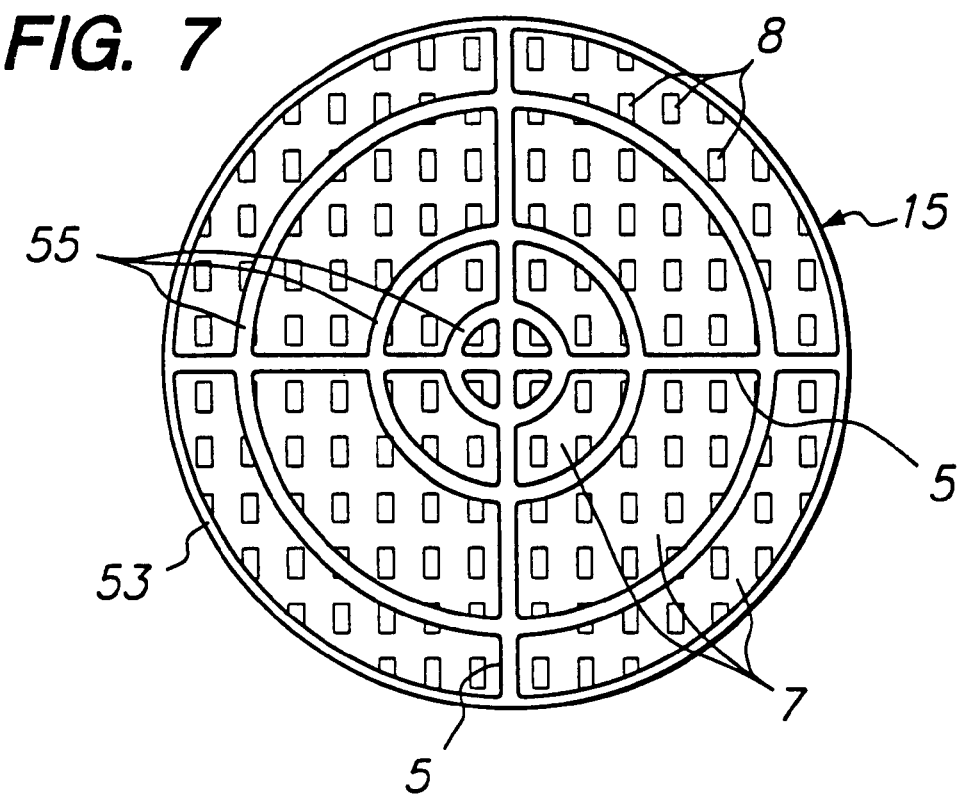

Various embodiments of the support member are illustrated in FIGS. 2 and 4–13. In the embodiments shown in FIGS. 2, 4–7 and 13, the support member 15 is comprised of a peripheral (e.g., annular) wall 53 having at least one cross-member 5 extending across the support member 15 so as to create a plurality of voids 7 which house the reservoir for the agent and to distribute an applied force substantially evenly across the sheet member 6 (i.e, without bending or flexing the sheet 6). The cross-members generally extend diagonally in FIGS. 4, 5, 6 and 13 across the volume bounded by the outer wall of the support member 15. Diagonal, as used herein, is meant to describe embodiments other than cross-members joining two vertices of a rectilinear figure that are nonadjacent or passing through two nonadjacent edges of a polyhedron, as is apparent from the embodiments shown in the figures. As can be seen, the cross-members include oblique (FIG. 6) and non-oblique (FIG. 7) cross-members as well as honeycomb configurations (FIG. 2). The number of cross-members depends on a variety of factors, for example, the relative structural integrity or flexibility of the sheet member 6 and the support member 15, the distance across the support member 15, the size of the agent reservoir skin-contact area, and the volume of the agent reservoir. In general, when using sheet member 6 formed of very thin metal, the maximum distance between adjacent cross-members 5 in support member 15 will be no more than about 4 times, and preferably no more than about 2 times, the distance between adjacent microprotrusions 4 in sheet member 6. FIG. 7 illustrates that the support member 15 can be comprised of a plurality of inner annular walls 55 connected by the cross-members 5 to the outer annular wall 53.

Figure 5:
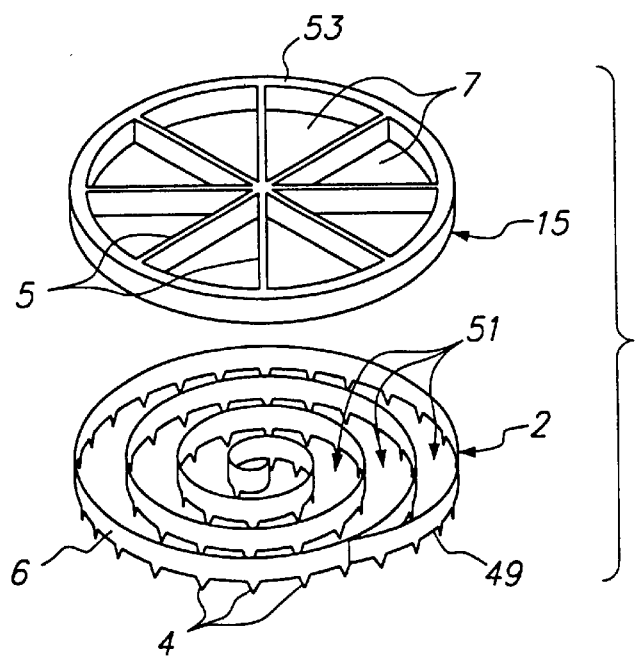
FIG. 5 is an exploded perspective view of an alternate embodiment of the rigid support and skin penetrating member.
Figure 6:
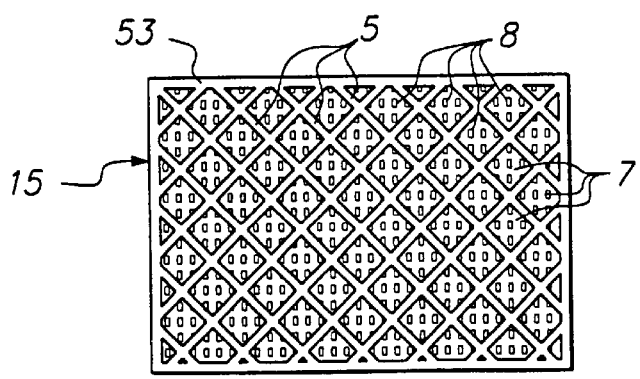

FIG. 5 illustrates an alternate embodiment of the sheet member 6 wherein the microprotrusions 4 extend outwardly from a body contacting edge 49 of a thin, sheet member 6. In this embodiment, the plane of the sheet member 6 is oriented in a roughly perpendicular relation to the body surface during use. The sheet member 6 has a spiral configuration which defines voids 51 for holding an agent-containing or an agent-receiving reservoir (not shown in FIG. 5). Coiling, folding (not shown), and curving (not shown) as well as other forms of forming the sheet member 6 from its generally planar state along its length to form a structure having a plurality of voids 51 can also be used. In a preferred embodiment, voids 51 are in communication with the voids 7 of the support member 15.

Figure 8:
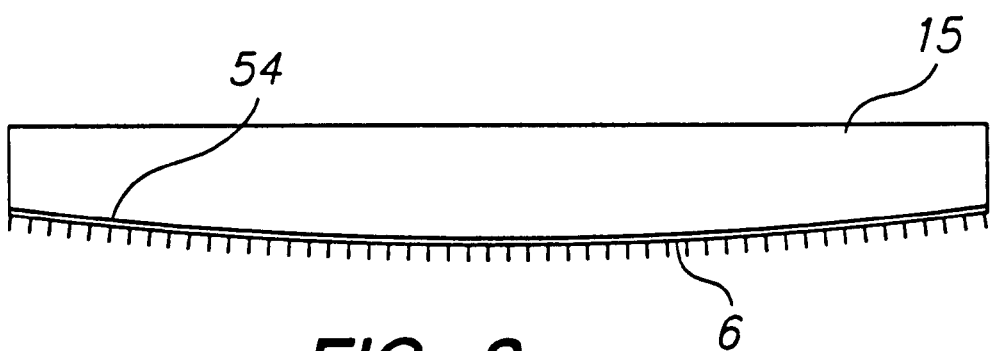
FIG. 8 is a side view of another embodiment of a support and skin penetrating member in accordance with the present invention.

The surface of support member 15 which contacts the skin distal side/edge of sheet member 6 is generally shown as flat (i.e., planar) in FIGS. 1 and 5. Most preferably however, the surface of support member 15 which contacts the sheet member 6 has a convex or curved (e.g., cylindrically shaped) surface 54 as best shown in FIG. 8. The radius of curvature of the convex or cylindrically shaped surface 54 is preferably more than about 5 cm, more preferably more than about 10 cm.

Figure 9:
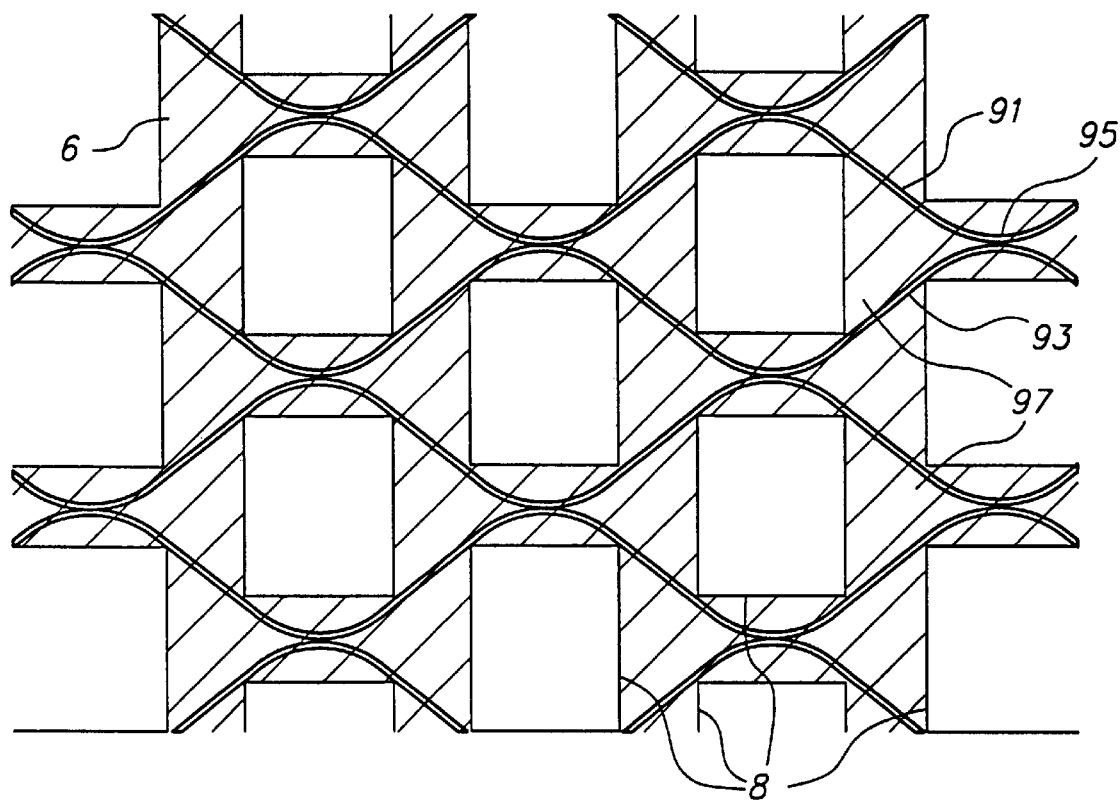
FIG. 9 is a top view of still another embodiment of the support member of the present invention.

FIG. 9 illustrates an alternate embodiment of the support member 15. In this embodiment, support member 15 is comprised of a plurality of strips which have a wavy shape and are oriented perpendicularly with respect to the plane of sheet member 6. Sheet member 6 has the same configuration shown in FIG. 3 with openings 8 therein and associated microprotrusions 4 (not shown in FIG. 9). The wavy strips 91, 93 are preferably fixed together at their contact points 95 such as by welding in the case where the sheets 91, 93 are composed of metal or plastic. The wavy configuration of the adjacent strips 91, 93 create voids 97 therebetween for containing an appropriate reservoir material. Thus, the height of strips 91 and 93 will be governed in part by the thickness of the reservoir material loaded into voids 97.

Figure 10:
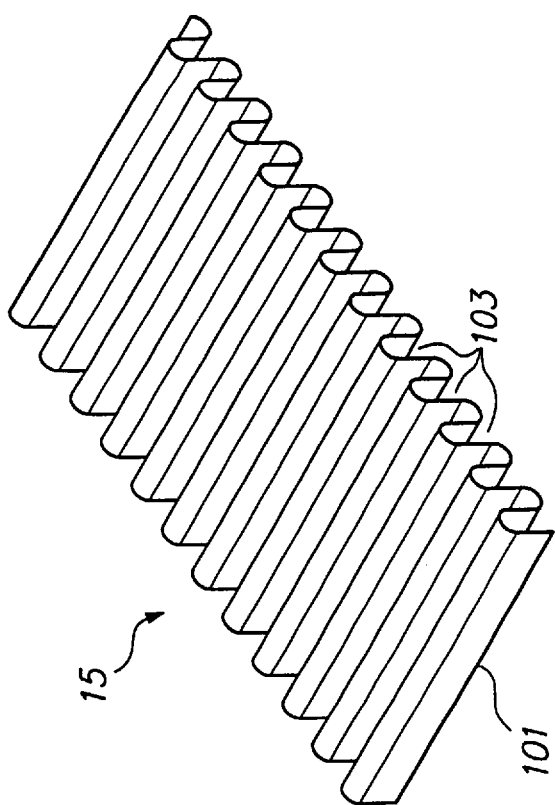
FIG. 10 is a perspective exploded view of yet another embodiment of the support of the present invention.

FIG. 10, illustrates yet another embodiment of the support member 15. In this embodiment, support member 15 is comprised of a corrugated sheet 101. Corrugated sheet 101 is adapted to contact the skin distal side of sheet member 6. If necessary, a cover sheet (not shown in FIG. 10) covering the skin distal side of corrugated sheet 101, or rails (not shown in FIG. 10) along the side edges of corrugated sheet 101, can be used to provide additional rigidity and to prevent any tendency for the sheet 101 to bend or fold along the corrugation folds when force is applied to the skin distal side of sheet 101. Optionally, corrugated sheet 101 may have a plurality of openings therein, thereby making it possible for agent to move through the corrugated sheet 101. The size and number of openings (not shown in FIG. 10) is not critical as long as the structural integrity and rigidity of the corrugated sheet 101 is not compromised. This would make it possible to place additional reservoir material into the voids 104 adjacent to the skin distal side of sheet 101. As in the other embodiments, a reservoir material can be loaded into the voids 103 formed between the corrugations and the underlying sheet member 6 (not shown in FIG. 10).

Figure 11:
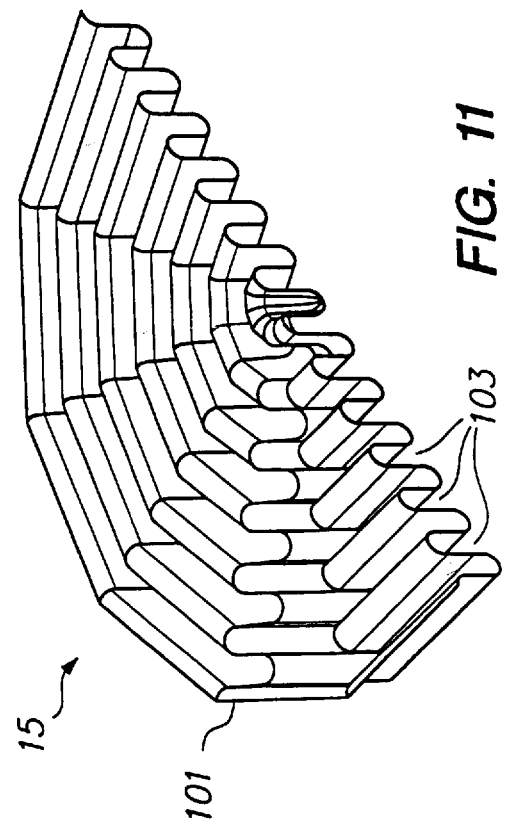
FIG. 11 is a sectional perspective exploded view of still another embodiment of the support of the present invention.

FIG. 11 discloses an alternate embodiment of a corrugated sheet 101 in which the corrugation folds are not all parallel to one another. Similar to the device of FIG. 10, the FIG. 11 device can also be provided, if necessary, with a covering sheet over the skin distal side of currugated sheet 101, or alternatively with an annular rail surrounding corrugated sheet 101, in order to enhance the structural rigidity of currugated sheet 101. Still further as in the FIG. 10 device, the FIG. 11 device can be provided with a plurality of openings (not shown in FIG. 11) in the corrugated sheet 101 in order to allow agent delivery therethrough. Such openings make it possible to utilize voids 104 to contain agent reservoir material.

A common feature of the support members 15 illustrated in FIG. 1–2, 4–7, 9–11 and 13 is that the support member 15 contains voids (e.g., voids 7,97 and 103) into which a reservoir material can be loaded. On the other hand, certain embodiments of the sheet member 6 such as that shown in FIG. 5 have their own voids 51 for containing the reservoir material. In cases such as this and also in cases where the sheet member 6 is applied to the skin as a pretreatment step prior to placing an agent-containing/sampling reservoir on the pretreated skin site, the support member 15 need not be integrally a part of or otherwise fixedly attached to the sheet member 6.

Figure 12:
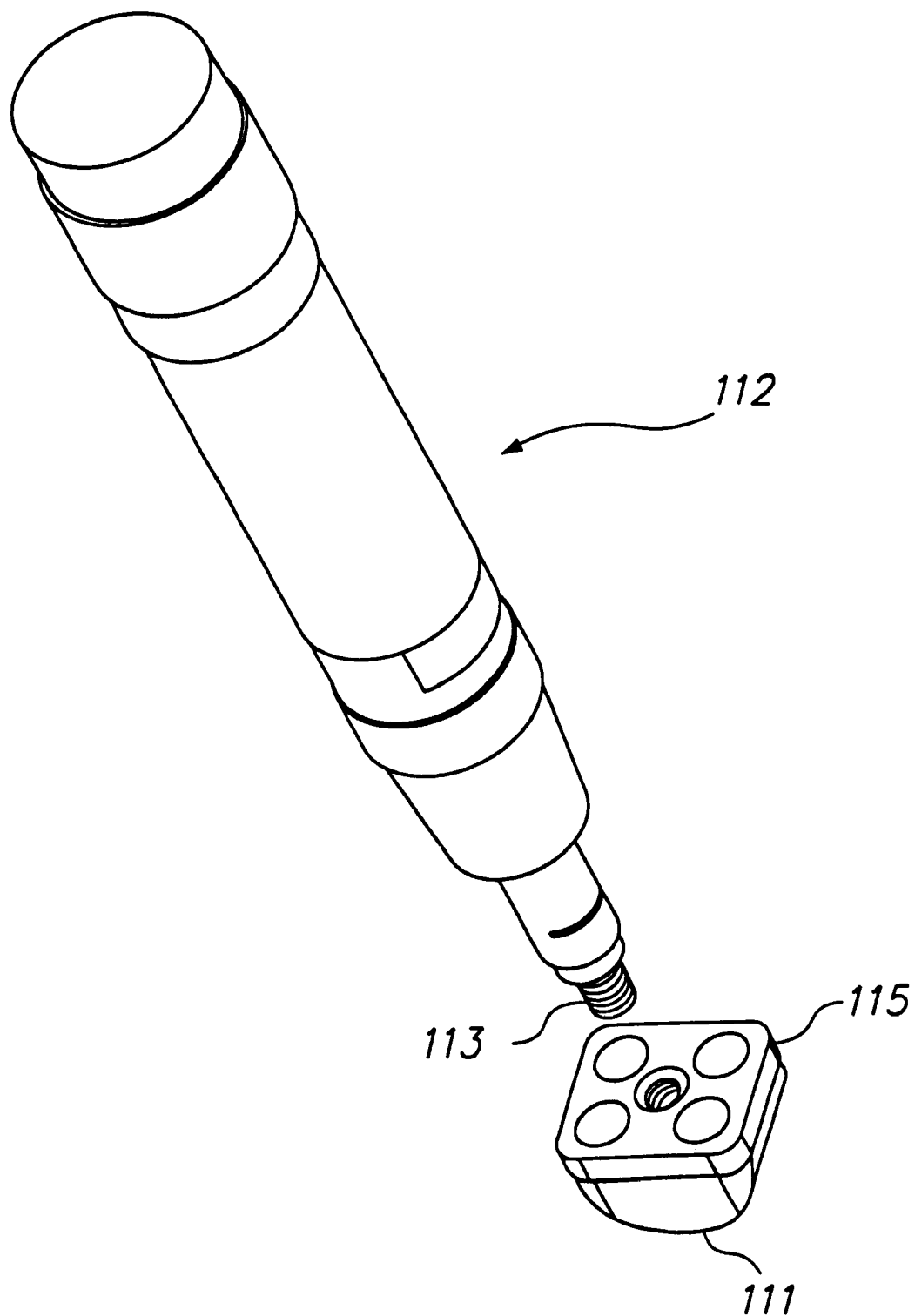
FIG. 12 is a perspective view of a hand-held device having a support in accordance with another embodiment of the present invention.
Figure 13:
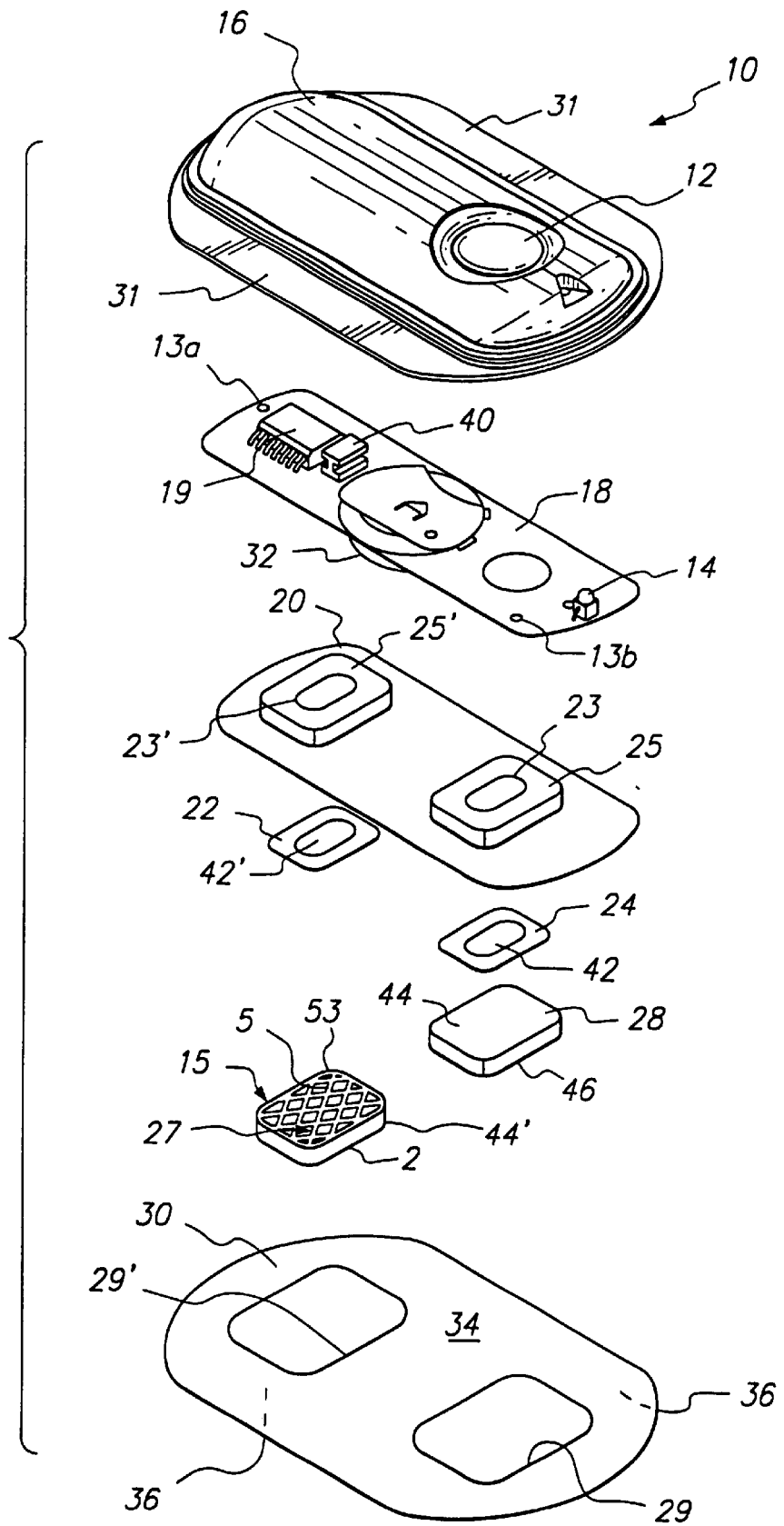
FIG. 13 is an exploded perspective view of one embodiment of an electrotransport agent delivery/sampling system according to one embodiment of the present invention.
Figure 14:
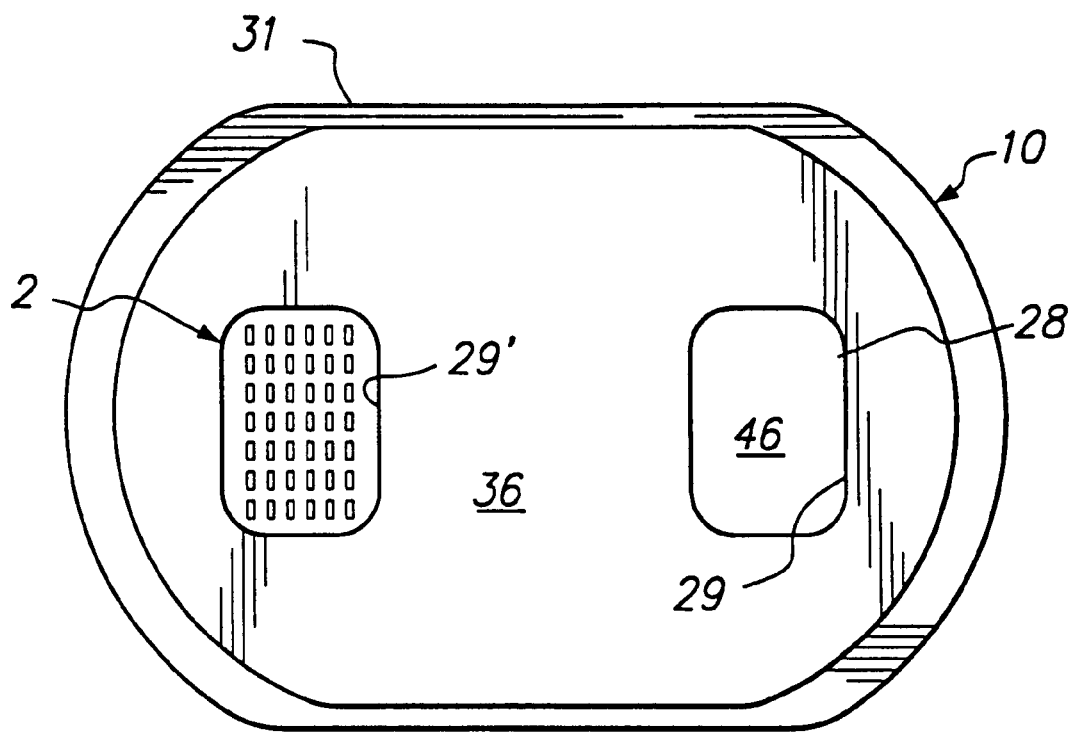
FIG. 14 is a bottom plan view of the electrotransport agent delivery/sampling system of FIG. 13.
Figure 15:
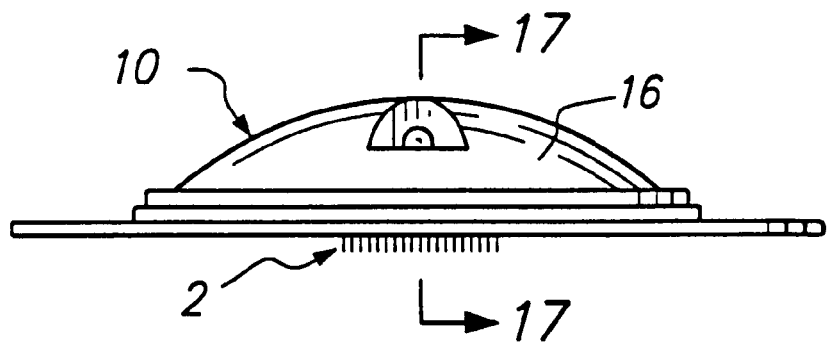
FIG. 15 is a right side elevational view of the electrotransport agent delivery/sampling system of FIG. 13.
Figure 16:
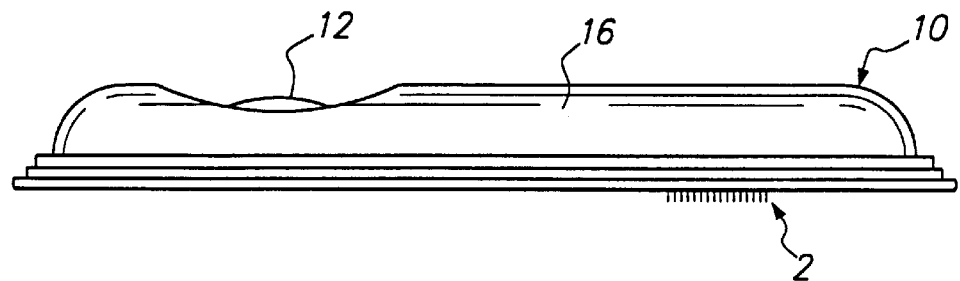
FIG. 16 is a rear elevational view of the electrotransport agent delivery/sampling system of FIG. 13.
Figure 17:
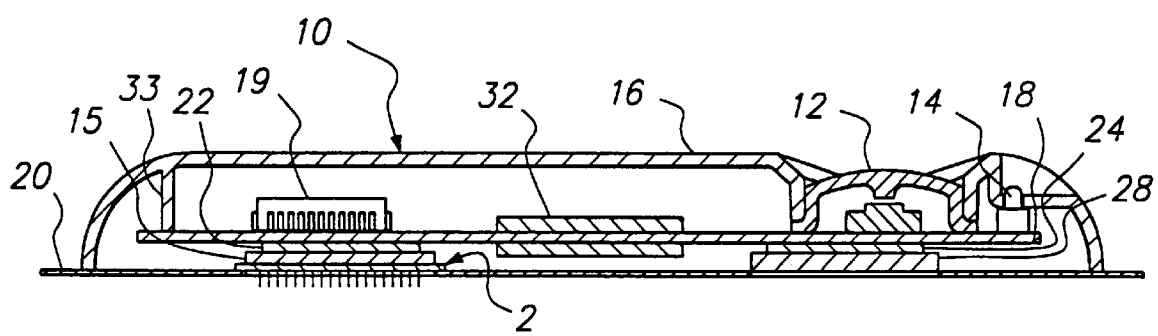
FIG. 17 is a cross-sectional view taken along line 17—17 of the assembled electrotransport agent delivery/sampling system of FIG. 15.

FIG. 12 illustrates a support member 115 which is the head of a hand-held device 112 used to press sheet member 6 into the skin. The head 115 is typically comprised of a metal plate having sufficient thickness (e.g., 0.5 cm or more) to impart sufficient rigidity thereto. The support member 115 is attached to device 112 by means of screw-threads 113. The surface 111 is pressed against the sheet member 6 in order to force the microprotrusions 4 to puncture the skin. Surface 111 may have either a convex curvature (as shown in FIG. 12 and as discussed earlier in connection with FIG. 8) or can be simply a flat (i.e., planar) surface. Optionally, device 112 can be spring-loaded in order to cause support member 115 to impact the skin distal side of sheet member 6 with a predetermined force.

Although the support member 15 of the present invention has been described primarily in connection with the initial application and piercing of body tissue (e.g., skin) by sheet member 6 and microprotrusion 4, those skilled in the art will appreciate that the rigid support member 15 is also useful for reapplication (i.e., subsequent application) of the sheet member 6 and subsequent piercing by the microprotrusions 4, either at the same body surface site as the first application or at a new body surface site. The subsequent piercing of the skin by the microprotrusions 4 at the original body surface site (i.e., the body surface site through which the microprotrusions 4 initially pierced) is useful in keeping the microcuts/microslits cut by the microprotrusions 4 open so that transdermal agent flux can continue unimpeded. Transdermal drug delivery/sampling devices, such as that disclosed in FIGS. 13–18, typically are adapted to adhere to the skin during transdermal delivery or sampling. After the microprotrusions 4 initially create microcuts/microslits through the stratum corneum, the skin immediately begins a healing process. Eventually, the microslits will close off as the healing process continues. Thus, reapplication of finger pressure to reapply the sheet member 6 against the skin is desirable in order to keep the microslits open and the transdermal agent flux unimpeded. This can be easily accomplished with the support structure of the present invention. When the transdermal delivery/sampling device is adhered to the skin, the patient or technician can simply periodically reapply finger or hand pressure to the skin distal side of the device in order to cause the microprotrusions 4 to repierce the stratum corneum.

The microprotrusions or microblades 4 are generally formed from a single piece of material and are sufficiently sharp and long for penetrating at least the stratum corneum of the skin. In one embodiment, the microprotrusions 4 and the sheet member 6 are essentially impermeable or are impermeable to the passage of an agent. The width of each microprotrusion can be any of a range of widths. The width of the microprotrusion at the intersection of the microprotrusion and the body surface after the microprotrusion array has been inserted is typically at least about 25 mm. The required length of the blades is subject to variation of the body surface being penetrated and corresponds to at least the natural thickness of the stratum corneum, for one of the principal features of the invention is that the microprotrusions are to penetrate at least through the stratum corneum and into the epidermis. Usually, the microprotrusions will have a length and configuration which achieves a depth of penetration of about 25 mm to about 400, with the depth of penetration for most applications being between about 50 mm to about 200 mm. The microprotrusions 4 can have slanted (i.e., angled) leading edges 64 (FIG. 3) to further reduce the insertion force required to press the microprotrusions into the skin tissue. The leading edges of each microprotrusion 4 can all be the same angle or can be at different angles suitable for penetrating the skin. Alternatively, the leading edge of each microprotrusion can be curved having, for example, a convex or concave shape or be divided into any number of angled segments such as the first segment being relatively steep with respect to vertical and the second segment being more gradually angled with respect to vertical.

The sheet member 6 can be produced with a photolithography process followed by a chemical etching process followed by a micropunching operation as disclosed in WO 97/48440, the disclosures of which are incorporated herein by reference. The embodiment of sheet member 6 illustrated in FIG. 5 requires an additional step of forming the planar sheet member 6 into the desired void-defining shape (i.e., spiral, serpentine, concentric circles, etc.). This can be accomplished using well-known metal sheet bending, rolling, folding and/or shaping techniques.

Generally, the microprotrusions 4 are at an angle of about 90° to the surface 48 (FIG. 3) of the sheet member 6 after being punched, but they can be disposed at any angle forward or backward from the perpendicular position that will facilitate penetration of the stratum corneum.

The sheet member 6 and microprotrusions 4 can be made from materials that have sufficient strength and manufacturability to produce microprotrusions, such as, glasses, ceramics, rigid polymers, reinforced (e.g., carbon fiber reinforced) polymers, metals and metal alloys. Examples of metals and metal alloys include but are not limited to stainless steel, iron, steel, tin, zinc, copper, gold, platinum, aluminum, germanium, zirconium, titanium and titanium alloys. Each of the sheet member and microprotrusions can have a thin layer of gold, platinum, iridium, titanium, or rhodium plating. Examples of glasses include silicas and devitrified glasses such as "PHOTOCERAM" available from Corning in Corning, N.Y. Examples of polymers include but are not limited to polystyrene, polymethylmethacrylate, polypropylene, polyethylene, "BAKELITE",cellulose acetate, ethylcellulose, styrene/acrylonitrile copolymers, stryrene/butadiene copolymers, acrylonitrile/butadiene/styrene (ABS) copolymers, polyvinyl chloride and acrylic acid polymers including polyacrylates and polymethacrylates.

The number of microprotrusions 4 and openings 8 of any of the embodiments of the sheet member 6 is variable with respect to the desired flux rate, agent being sampled or delivered, delivery or sampling device used (i.e., electrotransport, passive, osmotic, pressure driven, etc.), and other factors as will be evident to one of ordinary skill in the art. In general, the larger the number of microprotrusions per unit area (i.e., microblade density), the less concentrated the flux (per microslit) of the agent in the skin because there are a greater number of pathways through the skin. Consequently, a smaller number of microprotrusions per unit area leads to the transport of the agent through the skin becoming more concentrated in fewer pathways. Higher concentrations of agents in a skin pathway can lead to higher incidences and/or severity of skin reactions (e.g., irritation). Therefore, larger microblade densities reduce the incidence and/or severity of skin reactions.

An optional connecting medium (not shown) can be predisposed on the skin contacting side 48 of the sheet member 6 having the configuration shown in FIGS. 1–3 as taught in WO 98/28037, the disclosures of which are incorporate herein by reference. The connecting medium, if used, acts as a conduit for the agent and acts as a bridge between the agent containing or collecting reservoir and the skin, thus allowing an agent to be transported unhindered therethrough.

One type of transdermal delivery/sampling device, which can be used with the present invention relies on the application of an electric current across the body surface or "electrotransport". It will be appreciated by those working in the field that the present invention can be used in conjunction with a wide variety of electrotransport systems, as the invention is not limited in any way in this regard. For examples of electrotransport systems, reference may be had to U.S. Pat. Nos. 5,147,296 to Theeuwes et al., 5,080,646 to Theeuwes et al., 5,169,382 to Theeuwes et al., 5,423,739 to Phipps et al., 5,385,543 to Haak et al., 5,310,404 to Gyory et al., and 5,169,383 to Gyory et al., of which any of the disclosed electrotransport systems can be used with the present invention.

FIGS. 13–17 illustrate a representative electrotransport delivery/sampling device 10 that may be used in conjunction with a support member 15 and a skin penetrating device 2 in accordance with the present invention. Device 10 comprises an upper housing 16, a circuit board assembly 18, a lower housing 20, donor electrode 22, counter electrode 24, donor reservoir 27, counter reservoir 28 and skin-compatible adhesive 30. Upper housing 16 has lateral wings 31 which assist in holding device 10 on a patient's skin. Printed circuit board assembly 18 comprises an integrated circuit 19 coupled to discrete components 40 and battery 32. Circuit board assembly 18 is attached to housing 16 by posts 33 (only one shown in FIG. 17) passing through openings 13a and 13b, the ends of the posts being heated/melted in order to heat stake the circuit board assembly 18 to the housing 16. Lower housing 20 is attached to the upper housing 16 by means of adhesive layer 30, the upper surface 34 of adhesive layer 30 being adhered to both lower housing 20 and upper housing 16 including the bottom surfaces of wings 31. Shown (partially) on the underside of circuit board assembly 18 is a button cell battery 32. Other types of batteries may also be employed to power device 10 depending on the need.

The device 10 is generally comprised of battery 32, electronic circuitry 19,40, electrodes 22,24, counter reservoir 28, support member 15 housing donor reservoir 27, and skin penetrating device 2, all of which are integrated into a self-contained unit. Electrodes 22,24 and reservoirs 27,28 are retained by lower housing 20. The outputs (not shown in FIG. 13) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of reservoirs 27 and 28. The bottom side 46 of counter reservoir 28 contacts the patient's skin through the opening 29 in adhesive layer 30. The bottom side 46' of donor reservoir 27 contacts the patient's skin through the plurality of openings 8 in the skin penetrating device 2 as best shown in FIG. 1. The agent in donor reservoir 27 is typically in the form of a solution, most preferably an aqueous solution, which solution is contained in a solid matrix material such as a sponge, a hydrophilic polymer matrix (e.g., a hydrogel) which allows free mobility of the agent therethrough. The reservoir matrix material fills the openings 8 such that the agent reservoir is in contact with the body surface as can be seen in FIG. 1. As discussed above, a connecting medium can be placed as a layer on the skin-proximal side of sheet 6, with the microblades 4 passing therethrough. The optional connecting medium provides a more consistent agent flow pathway between the donor reservoir 27 and the skin. Typically the agent is present initially in both the reservoir and the connecting medium because of diffusion or because the reservoir and connecting medium are the same material.

The device 10 adheres to the patient's body surface (e.g., skin) by means of a peripheral adhesive layer 30 (which has upper adhesive side 34 and body-contacting adhesive side 36) and, optionally, anchoring elements on the device 2 of any of the embodiments discussed herein. Further, optionally, the connecting medium 65 can be tacky or adhesive for assisting in maintaining interface contact with the skin. The adhesive side 36 covers the entire underneath side of the device 10 except where the device 2 and counter electrode reservoir 28 are located. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and agent reservoirs within housing depression 25, 25' as well as retains device 2 to lower housing 20 and lower housing 20 to upper housing 16.

In one embodiment of the agent delivery/sampling device there is a release liner (not shown) on the device 10 for maintaining the integrity of adhesive layer 30 when the device is not in use. In use, the release liner is stripped from the device before the device is applied to the skin. Device 10 also has a push button switch 12, which when pressed turns the device 10 on which is made apparent to the user by means of LED 14 becoming lit. Agent is delivered through the patient's skin (e.g., on the arm) by electrotransport over a predetermined delivery interval.

Figure 18:
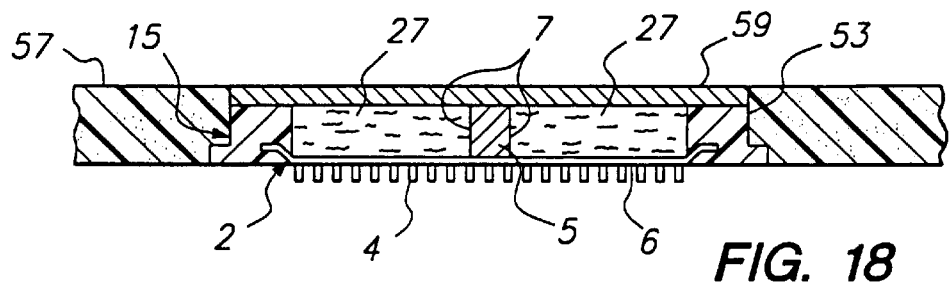
FIG. 18 is a diagrammatic cross-sectional view of a passive agent delivery/sampling system in accordance with one embodiment of the present invention.

In other embodiments of the present invention, passive transdermal delivery or sampling devices are used with the support member 15 predisposed on the top surface of the member 6. It will be appreciated by those working in the field that the present invention can be used in conjunction with a wide variety of passive transdermal systems, as the invention is not limited in this regard. For examples of passive systems, reference may be had to, but not limited to, U.S. Pat. Nos. 4,379,454 to Campbell, et al., 4,588,580 to Gale et al., 4,832,953 to Campbell et al., 4,698,062 to Gale et al., 4,867,982 to Campbell et al., and 5,268,209 to Hunt et al., of which any of the disclosed systems can be used with the present invention. One example of a passive transdermal delivery/sampling device is illustrated in FIG. 18. Support member 15 having the edges of sheet member 6 embedded in the outer annular wall 53 thereof is housed in a foam pad or band 57 which can be applied to the body surface. The edges of sheet member 6 need not be embedded in the outer annular wall, as the sheet member 6 can be attached to the support member 15 as described in the previous embodiments. Extending across annular wall 53 and cross-member 5 is a rigid top 59. Top 59 is sufficiently rigid so as not to deform when force is applied thereto and so as to more evenly transmit the applied force and displacement of microprotrusions 4 across the length and width of sheet member 6. Preferably, although not required, the passive delivery/sampling device has a peripheral adhesive on the body-contacting surface of foam pad 57 and an adhesive interface gel (not shown) on the body-contacting side of the member 2.

It will be appreciated by those working in the field that the present invention can also be used in conjunction with a wide variety of osmotic and pressure driven systems, as the invention is not limited to a particular device in this regard. For examples of osmotic and pressure driven devices, reference may be had to U.S. Pat. Nos. 4,340,480 to Eckenhoff, 4,655,766 to Theeuwes et al., 4,753,651 to Eckenhoff, 5,279,544 to Gross et al., 4,655,766 to Theeuwes, 5,242,406 to Gross et al., and 4,753,651 to Eckenhoff any of which can be used with the present invention.

This invention has utility in connection with the delivery of agents within any of the broad class of drugs normally delivered through body surfaces and membranes, including skin. In general, this includes drugs in all of the major therapeutic areas. The invention is also useful in the transdermal delivery of proteins, peptides and fragments thereof, whether naturally occurring, chemically synthesized or recombinantly produced. The invention may additionally be used in conjunction with the delivery of vaccines, nucleotidic drugs, including oligonucleotide drugs, polynucleotide drugs, and genes. These substances typically have a molecular weight of at least about 300 daltons, and more typically have a molecular weight of at least about 300 to 40,000 daltons. As mentioned, the device 2 of the present invention can also be used with sampling devices including, but not limited to, reverse electrotransport (i.e., reverse iontophoresis and/or reverse electroosmosis in the case of sampling uncharged materials such as glucose), osmosis, and passive diffusion. For example, reference may be had to U.S. Pat. Nos. 4,756,314 to Eckenhoff et al., 5,438,984 to Schoendorfer, 5,279,543 to Glikfeld et al., and 5,362,307 to Guy et al.

It will be appreciated by those of ordinary skill in the art that the invention can be embodied in other specific forms without departing from the spirit or essential character thereof. The presently disclosed embodiments are therefore considered in all respects to be illustrative and not restrictive. The scope of the invention is indicated by the appended claims rather than the foregoing description, and all changes which come within the meaning and range of equivalents thereof are intended to be embraced therein.

What is claimed is:

1. A device for use in introducing or withdrawing an agent through a body surface, comprising:
   a thin, flexible sheet-like member having a plurality of microprotrusions extending from a body surface proximal portion of the member; and
   a structural support which defines one or more voids for an agent-containing or agent receiving reservoir and which extends substantially across, and makes contact substantially across, a width, length and/or diameter of the member, the support having greater rigidity than the member and wherein the structural support substantially reduces the tendency of the member to deflect upon application of a force to the top of the structural support.

2. The device of claim 1, wherein the support has greater rigidity to a force applied perpendicular to the body surface than does the member.

3. The device of claim 1, wherein the support is sufficiently rigid to deflect less than 300 $\mu$m under manually applied finger or hand pressing of the device against skin.

4. The device of claim 3, wherein the support deflects less than 50 $\mu$m under said pressing.

5. The device of claim 1, wherein the support is sufficiently incompressible to compress less than 250 $\mu$m under manually applied finger or hand pressing of the device against skin.

6. The device of claim 5, wherein the support compresses less than 50 $\mu$m under said pressing.

7. The device of claim 1, wherein the member comprises a sheet which in use is oriented approximately parallel to the body surface, the sheet having a plurality of openings therein and the plurality of microprotrusions extending from a body proximal surface of the sheet, said microprotrusions being adapted to pierce the body surface.

8. The device of claim 1, wherein the structural support comprises a plurality of cross-members, the cross-members being spaced no more than about 4 times a distance between adjacent microprotrusions in said microprotrusion member.

9. The device of claim 7, wherein the reservoir is in agent-transmitting communication with the openings in the sheet.

10. The device of claim 1, wherein the support comprises a peripheral member and a plurality of cross-members.

11. The device of claim 1, wherein the support has a honeycomb structure.

12. The device of claim 1, wherein the support comprises a corrugated sheet.

13. The device of claim 1, wherein the support has a curved surface which contacts the member.

14. The device of claim 13, wherein the curved surface has a shape selected from the group consisting of convex and cylindrical.

15. The device of claim 7, wherein the support comprises a plurality of wavy strips arranged in perpendicular alignment to the sheet.

16. The device of claim 1, wherein the member has a thickness of less than 100 µm.

17. The device of claim 16, wherein the member is comprised of metal.

18. The device of claim 1, wherein the member comprises a sheet having the plurality of microprotrusions extending from a body surface proximal edge of the sheet for piercing the body surface, the sheet when in use being oriented in an approximately perpendicular relation to the body surface with the body surface proximal edge having the microprotrusions engaging the body surface.

19. The device of claim 18, wherein the sheet has a configuration which defines a void for an agent-containing or agent-receiving reservoir.

20. The device of claim 18, wherein the support contacts a second edge of the sheet, which second edge is opposite to the body surface proximal edge having microprotrusions.

21. A method of maintaining open agent-transmitting pathways through a body surface having the device of claim 1 positioned adjacent thereto, comprising periodically reapplying a body surface directed force to said device.

22. The method of claim 21, wherein said reapplying causes said microprotrusions to repierce the body surface.

23. The method of claim 21, wherein said force is applied manually.

24. The method of claim 21, wherein the structural support comprises an annular member.

25. The method of claim 24, wherein the annular member is a circular, square or rectangular annular member having a diagonal cross-member.

26. The method of claim 21, wherein the structural support has a plurality of cross-members.

27. The method of claim 26, wherein the plurality of cross-members intersect generally in the center of the structural support.

28. The method of claim 21, wherein the structural support comprises:
an outer annular member;
an inner annular member having a diameter less than a diameter of the outer annular member; and
the cross-member joins the inner annular member to the outer annular member.

29. The method of claim 21, wherein the support has greater rigidity to a force applied perpendicular to the body surface than does the member.

30. The method of claim 21, wherein the support is sufficiently rigid to deflect less than 300 µm under manually applied finger or hand pressing of the device against skin.

31. The method of claim 30, wherein the support deflects less than 50 µm under said pressing.

32. The method of claim 21, wherein the support is sufficiently incompressible to compress less than 250 µm under manually applied finger or hand pressing the device against skin.

33. The method of claim 32, wherein the support compresses less than 50 µm under said pressing.

34. The method of claim 21, wherein the member comprises a sheet which in use is oriented approximately parallel to the body surface, the sheet having a plurality of openings therein and the plurality of microprotrusions extending from a body proximal surface of the sheet, said microprotrusions being adapted to pierce the body surface.

35. The method of claim 21, wherein the structural support defines a void for an agent-containing or agent-receiving reservoir.

36. The device of claim 1, wherein the member has one or more peripheral edges and an interior portion surrounded by the one or more peripheral edges, wherein the structural support extends from the one or more peripheral edges and across the interior portion of the member.

37. The device of claim 8, wherein the cross-members define a plurality of voids for an agent-containing or agent-receiving reservoir.

* * * * *

UNITED STATES PATENT AND TRADEMARK OFFICE
CERTIFICATE OF CORRECTION

PATENT NO.     : 6,322,808 B1
DATED          : November 27, 2001
INVENTOR(S)    : Joseph Creagan Trautmann et al.

It is certified that error appears in the above-identified patent and that said Letters Patent is hereby corrected as shown below:

Title page,
Insert item:
-- Related U.S. Application Data
[60] U.S. Provisional Application No. 60/069,339 filed on December 11, 1997 --

Column 1,
After the Title, please insert:
          -- CROSS REFERENCE TO RELATED APPLICATIONS This application claims benefit, under 35 USC 119(e), to U.S. provisional patent application number 60/069,339 filed December 11, 1997. --

Signed and Sealed this

Twentieth Day of April, 2004

JON W. DUDAS
*Acting Director of the United States Patent and Trademark Office*